(12) United States Patent
Tu et al.

(10) Patent No.: US 9,335,263 B2
(45) Date of Patent: May 10, 2016

(54) OPTICAL CIRCUIT FOR SENSING A BIOLOGICAL ENTITY IN A FLUID AND METHOD OF CONFIGURING THE SAME

(71) Applicant: Agency for Science, Technology and Research, Singapore (SG)

(72) Inventors: Xiaoguang Tu, Singapore (SG);
Tsung-Yang Liow, Singapore (SG);
Mingbin Yu, Singapore (SG);
Guo-Qiang Lo, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 654 days.

(21) Appl. No.: 13/623,353

(22) Filed: Sep. 20, 2012

(65) Prior Publication Data

US 2013/0071061 A1 Mar. 21, 2013

(30) Foreign Application Priority Data

Sep. 21, 2011 (SG) .............................. 201106834-3

(51) Int. Cl.
*G02B 6/00* (2006.01)
*G01N 21/45* (2006.01)
*G01N 21/41* (2006.01)
*G02B 6/12* (2006.01)

(52) U.S. Cl.
CPC ................ *G01N 21/45* (2013.01); *G01N 21/41* (2013.01); *G01N 2021/458* (2013.01); *G02B 6/12007* (2013.01); *G02B 2006/12159* (2013.01)

(58) Field of Classification Search
None
See application file for complete search history.

(56) References Cited

U.S. PATENT DOCUMENTS

| 6,256,442 | B1* | 7/2001 | Nolan et al. .................. 385/129 |
| 6,618,536 | B1 | 9/2003 | Heideman et al. |
| 2003/0152304 | A1* | 8/2003 | Gonthier et al. .................. 385/1 |
| 2004/0239944 | A1* | 12/2004 | Shirai et al. .................... 356/481 |
| 2005/0135723 | A1* | 6/2005 | Carr et al. ........................ 385/12 |
| 2010/0165351 | A1* | 7/2010 | Xu et al. ......................... 356/477 |
| 2011/0102804 | A1* | 5/2011 | Lipson et al. ................. 356/480 |
| 2011/0292398 | A1* | 12/2011 | Klein Koerkamp et al. .. 356/477 |

OTHER PUBLICATIONS

Yanik, et al., An Optofluidic Nanoplasmonic Biosensor for Direct Detection of Live Viruses form Biological Media, Nano Letters 4962 (2010).
Vos, et al., Optical Biosensor Based on Silicon-on-Insulator Microring Cavities for Specific Protein Binding Detection, 6447 Proceedings of SPIE. (2007).
Liedberg, et al., Biosensing with Surface Plasmon Resonance-How it all Started, 10 Biosensors and Bioelectronics (1995).

(Continued)

*Primary Examiner* — Hemang Sanghavi
(74) *Attorney, Agent, or Firm* — K. David Crockett, Esq.; Niky Economy Syrengelas, Esq.; Crockett & Crockett, PC

(57) ABSTRACT

An optical circuit for sensing a biological entity in a fluid and a method of configuring an optical circuit for sensing a biological entity in a fluid are provided. The optical circuit includes a sensing arrangement including a reference arm having a reference waveguide and a sensing arm having a waveguide; wherein lengths of the reference waveguide and the waveguide are configured in accordance with a temperature dependency reduction criterion.

20 Claims, 16 Drawing Sheets

(56) References Cited

OTHER PUBLICATIONS

DKK-TOA Corporation, Surface Plasmon Resonance Sensor, http://www.dkktoa.net/productslpi4.html.

Reichert Technologies, http://www.reichert.com/index.cfm.

GE Healthcare, http://www2.gehealthcare.com/portal/site/usen/.

Jetalon Solutions, Inc., http://www.jetalon.com.

Carlborg, et al., A Packaged Optical Slot-Waveguide Ring Resonator Sensor Array for Multiplex Label-Free Assays in Labs-on-Chips, 10 Lab on Chip, 281 (2010).

Claes, et al., Experimental Characterization of a Silicon Photonic Biosensor Consisting of Two Cascaded Ring Resonators Based on the Vernier-Effect and Introduction of a Curve Fitting Method for an Improved Detection Limit, 18 Optics Express, 22747 (2010).

Uenuma, et al., Temperature-Independent Silicon Waveguide Optical Filter, 34 Optics Letters, (2009).

Teng, et al., Athermal Silicon-on-Insulator Ring Resonators by Overlaying a Polymer Cladding on Narrowed Waveguides, 17 Optics Express, 14627 (2009).

Xu, et al., Real-Time Cancellation of Temperature Induced Resonance Shifts in SOI Wire Waveguide Ring Resonator Laber-Free Biosensor Arrays, 18 Optics Express, 22867 (2010).

* cited by examiner

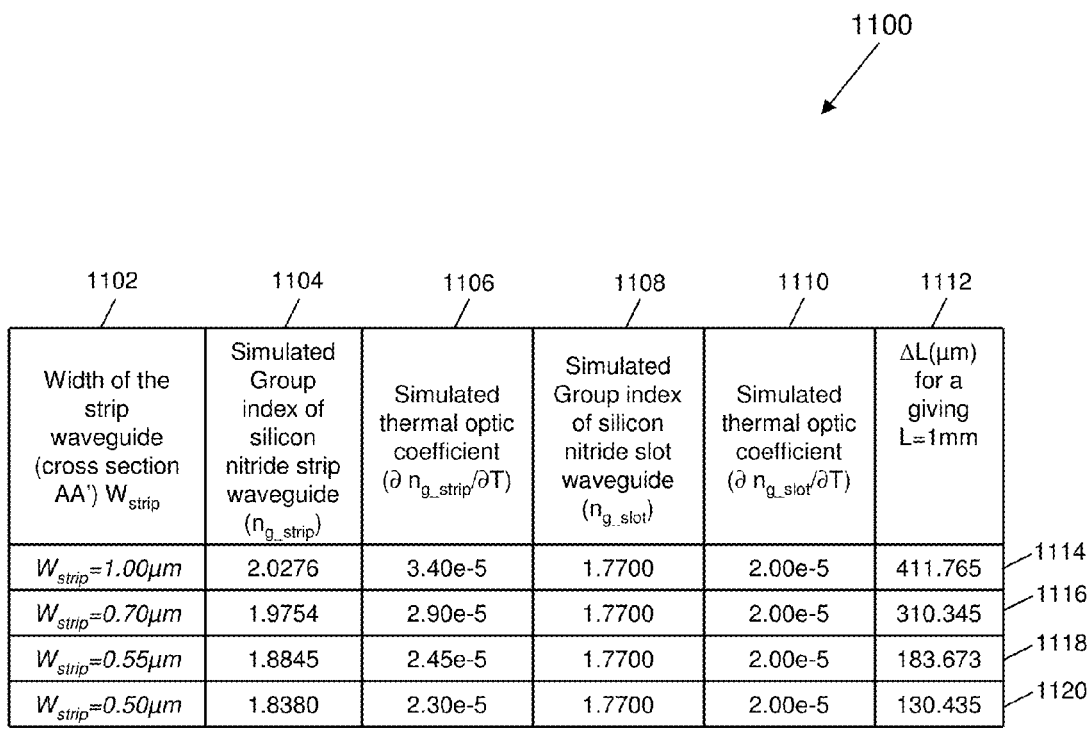

| Width of the strip waveguide (cross section AA') $W_{strip}$ | Simulated Group index of silicon nitride strip waveguide ($n_{g\_strip}$) | Simulated thermal optic coefficient ($\partial n_{g\_strip}/\partial T$) | Simulated Group index of silicon nitride slot waveguide ($n_{g\_slot}$) | Simulated thermal optic coefficient ($\partial n_{g\_slot}/\partial T$) | $\Delta L(\mu m)$ for a giving $L=1mm$ |
|---|---|---|---|---|---|
| $W_{strip}=1.00\mu m$ | 2.0276 | 3.40e-5 | 1.7700 | 2.00e-5 | 411.765 |
| $W_{strip}=0.70\mu m$ | 1.9754 | 2.90e-5 | 1.7700 | 2.00e-5 | 310.345 |
| $W_{strip}=0.55\mu m$ | 1.8845 | 2.45e-5 | 1.7700 | 2.00e-5 | 183.673 |
| $W_{strip}=0.50\mu m$ | 1.8380 | 2.30e-5 | 1.7700 | 2.00e-5 | 130.435 |

| Width of the strip waveguide (cross section AA') $W_{strip}$ | FSR1 (nm) of the sensing MZI with $L_{sen}$=7mm | $\Delta L_{sen}$(μm) for a giving $L_{sen}$=7mm in the sensing MZI | FSR2 (nm) of the reference MZI | $L_{ref}$ (mm) in the reference MZI |
|---|---|---|---|---|
| $W_{strip}$=1.00μm | 0.54 | 2,882.355 | 0.52 | 25.2884 |
| | | | 0.54 | 24.3518 |
| | | | 0.56 | 23.4821 |

Figure 12

OPTICAL CIRCUIT FOR SENSING A BIOLOGICAL ENTITY IN A FLUID AND METHOD OF CONFIGURING THE SAME

This application claims the benefit of priority of Singapore Patent Application No. 201106834-3, filed Sep. 21, 2011, the entire contents of which are incorporated herein by reference for all purposes.

FIELD OF THE INVENTIONS

Various embodiments relate generally to an optical circuit for sensing a biological entity in a fluid and a method of configuring an optical circuit for sensing a biological entity in a fluid.

BACKGROUND OF THE INVENTIONS

Refractive index optical biosensor can be used in applications such as drinking water contaminations monitor, early detection of infectious viral diseases and real-time study of molecular interaction in chemical and biological processes. Generally, sensors with a high sensitivity have a high sensitivity to temperature. Thus, temperature of a testing condition can greatly influence the measured results of the sensors. However, conventional approach of using polymer negative thermal optic (TO) cladding to overcome this problem cannot be utilized in biosensors.

In the market of optical refractive index biosensor, one widely used method is through surface plasmon resonance (SPR). Surface Plasmon is a charge density wave occurring at the interface between a metal and a dielectric. It can be stimulated when a beam of light is incident on the interface of a metal layer and the biochemical target with a certain angle between the light and the surface. This angle can be shifted according to the change of the refractive index of the biochemical. By monitoring the incident angle or the intensity of the reflected light, this change of the refractive index can be achieved. The simplicity of experimental set-up and the reasonable sensitivities obtained using surface plasmon made this technology a practical and commonly used method in the application of biosensor. The SPR biosensor can provide the following of biospecific interactions in real time instead of the determining of the concentration of the target chemical. However, the size and cost of the instrument are still very large which limited the application of the SPR biosensor.

Silicon photonics can offer a platform for the chip-size integration of these big components with more functions and lower cost. For example, the incident light prism coupling method in SPR biosensor can be replaced by etching grating coupler on the surface of the silicon chip for fiber coupling. The complex optical routes set up in SPR biosensor can be replaced by standard plane waveguide routes on Silicon-On-Insulator and the big-size output signals collection part in the SPR biosensor can also be replaced by integrating germanium photo detectors on the same chip with that of biosensor. The advantages of shrinking the biosensor to chip size can include automation of the analysis, shorter response time, reduced manual sampling handling and low cost. Utilizing silicon photonics platform, volume refractive index and surface mass density detection limit of biosensor made on array of silicon nitride slot waveguide micro-ring resonators may reach 5.0e-6 refractive index units (RIUs) and 0.9 pg/mm$^2$ respectively. However, the impact of temperature is more serious in silicon waveguide-based biosensors because of the large thermal-optical effect of the silicon material. Micro-ring resonators may help to increase the sensitive of the sensor but the measure error coming from environment temperature may become larger. Thermal drift may be compensated using on-chip referencing, external thermal modulator or Peltier heat pump in the platform. However, the complexity and cost may be increased at the same time.

SUMMARY

According to one embodiment, an optical circuit for sensing a biological entity in a fluid is provided. The optical circuit includes a sensing arrangement including a reference arm having a reference waveguide and a sensing arm having a waveguide; wherein lengths of the reference waveguide and the waveguide are configured in accordance with a temperature dependency reduction criterion.

According to another embodiment, a method of configuring an optical circuit for sensing a biological entity in a fluid is provided. The optical circuit includes a sensing arrangement including a reference arm having a reference waveguide and a sensing arm having a waveguide. The method includes determining lengths of the reference waveguide and the waveguide based on a temperature dependency reduction criterion.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIG. 11 shows a table listing main parameters of an optical circuit according to one embodiment.

FIG. 12 shows a table listing main parameters of an optical circuit according to one embodiment.

DETAILED DESCRIPTION OF THE INVENTIONS

Embodiments of an optical circuit for sensing a biological entity in a fluid and a method of configuring an optical circuit for sensing a biological entity in a fluid will be described in detail below with reference to the accompanying figures. It will be appreciated that the embodiments described below can be modified in various aspects without changing the essence of the invention.

Figure 1:
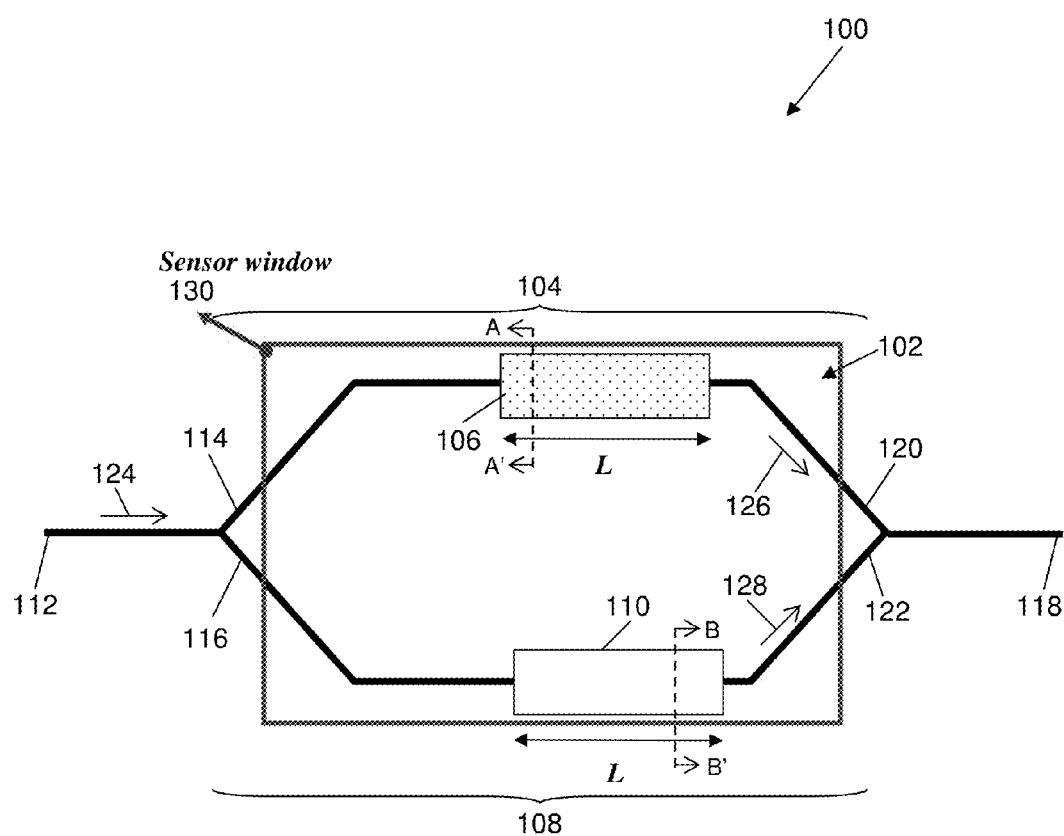
FIG. 1 shows a schematic diagram of an optical circuit for sensing a biological entity in a fluid according to one embodiment.

FIG. 1 shows a schematic diagram of an optical circuit 100 for sensing a biological entity in a fluid according to one embodiment. The optical circuit 100 includes a sensing arrangement 102 including a reference arm 104 having a reference waveguide 106 and a sensing arm 108 having a waveguide 110.

Figure 2:
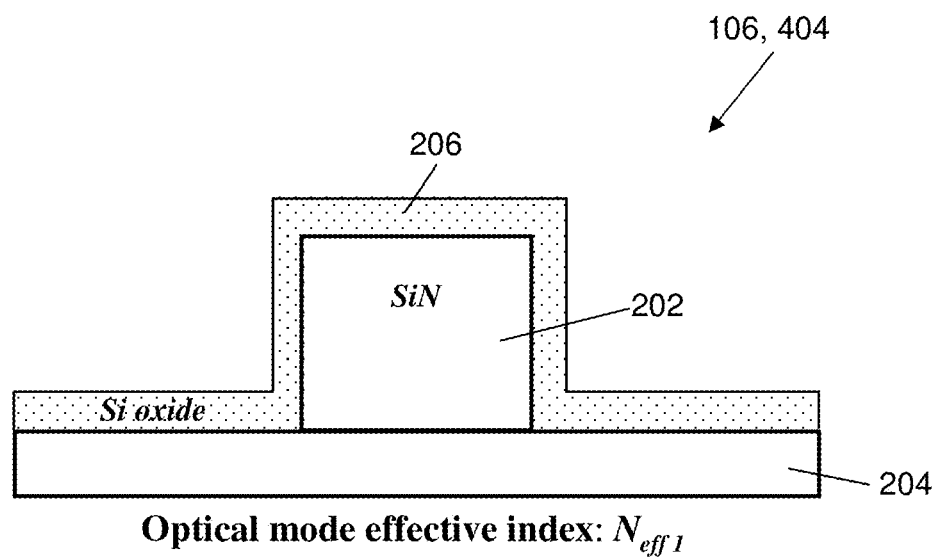
FIG. 2 shows a cross-sectional view of a reference waveguide of an optical circuit according to one embodiment.

FIG. 2 shows a cross-sectional view of the reference waveguide 106 along line A-A'. The reference waveguide 106 has a core layer 202 disposed above a first cladding layer 204. The reference waveguide 106 has a second cladding layer 206 disposed above the core layer 202 and the first cladding layer 204. The core layer 202 includes at least one of silicon nitride and silicon (e.g. silicon nitride, silicon or a combination of silicon nitride and silicon). The first cladding layer 204 may have the same materials as the core layer 202. The second cladding layer 206 includes silicon oxide.

Figure 3:
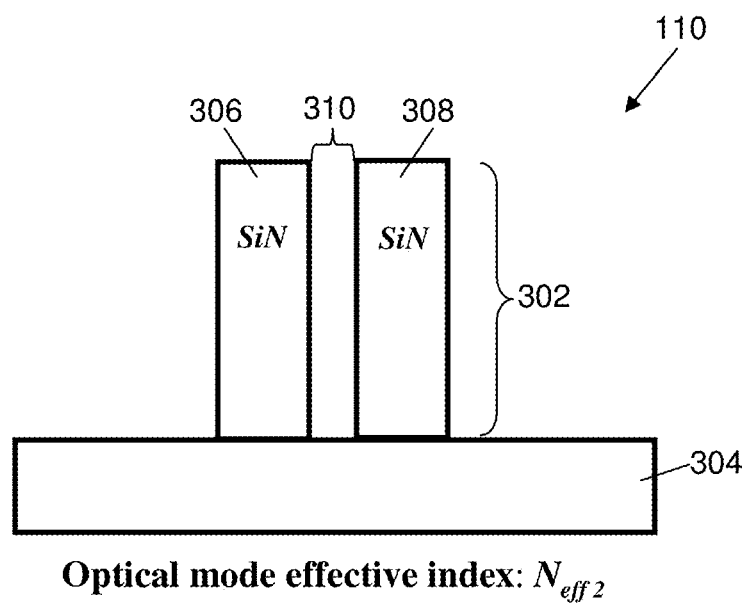
FIG. 3 shows a cross-sectional view of a waveguide of an optical circuit according to one embodiment.

FIG. 3 shows a cross-sectional view of the waveguide 110 along line B-B'. The waveguide 110 of the sensing arm 108 has a core layer 302 disposed above a cladding layer 304. The core layer 302 of the waveguide 110 has a first portion 306 and a second portion 308. The first portion 306 of the core layer 302 is arranged adjacent to the second portion 308 of the core layer 302 such that a slot 310 is formed between the first portion 306 and the second portion 308. The core layer 302 includes at least one of silicon nitride and silicon (e.g. silicon nitride, silicon or a combination of silicon nitride and silicon). In one embodiment, the waveguide 110 is a slot waveguide.

Referring back to FIG. 1, the sensing arrangement 102 further includes an input port 112 coupled to a first end 114 of the reference arm 104 and a first end 116 of the sensing arm 108. The sensing arrangement 102 includes an output port 118 coupled to a second end 120 of the reference arm 104 and a second end 122 of the sensing arm 108. The input port 112 is configured to direct an optical signal 124 to the first end 114 of the reference arm 104 and the first end 116 of the sensing arm 108. The output port 118 is configured to combine an optical signal 126 from the second end 120 of the reference arm 104 and an optical signal 128 from the second end 122 of the sensing arm 108.

In one embodiment, the sensing arrangement 102 may be used as a sensing Mach Zehnder interferometer (MZI). The sensing arrangement 102 may contact e.g. a micro-fluid of a target chemical. The reference arm 104 having the reference waveguide 106 and the sensing arm 108 having the waveguide 110 are disposed in a sensing window 130 of the optical circuit 100. In other words, the sensing arrangement 102 has a sensing window 130 extending across the reference arm 104 and the sensing arm 108. The components in the sensing window 130 contact e.g. the micro-fluid of the target chemical. The waveguide 110 may be a biosensing waveguide.

Lengths of the reference waveguide 106 and the waveguide 110 are configured in accordance with a temperature dependency reduction criterion. Thus, the sensing arrangement 102 may be temperature independent or the temperature dependency of the sensing arrangement 102 may be reduced. The lengths of the reference waveguide 106 and the waveguide 110 are further configured in accordance with refractive indices of the reference waveguide 106 ($n_{eff1}$) and the waveguide 110 ($n_{eff2}$). In one embodiment, the reference waveguide 106 and the waveguide 110 have the same length (L).

In one embodiment, the sensing arrangement 102 may be temperature-independent by proper design including the cross-section dimensions and lengths of the reference arm 104 and the sensing arm 108 (e.g. the cross-section dimensions and lengths of the reference waveguide 106 and the waveguide 110).

Figure 4:
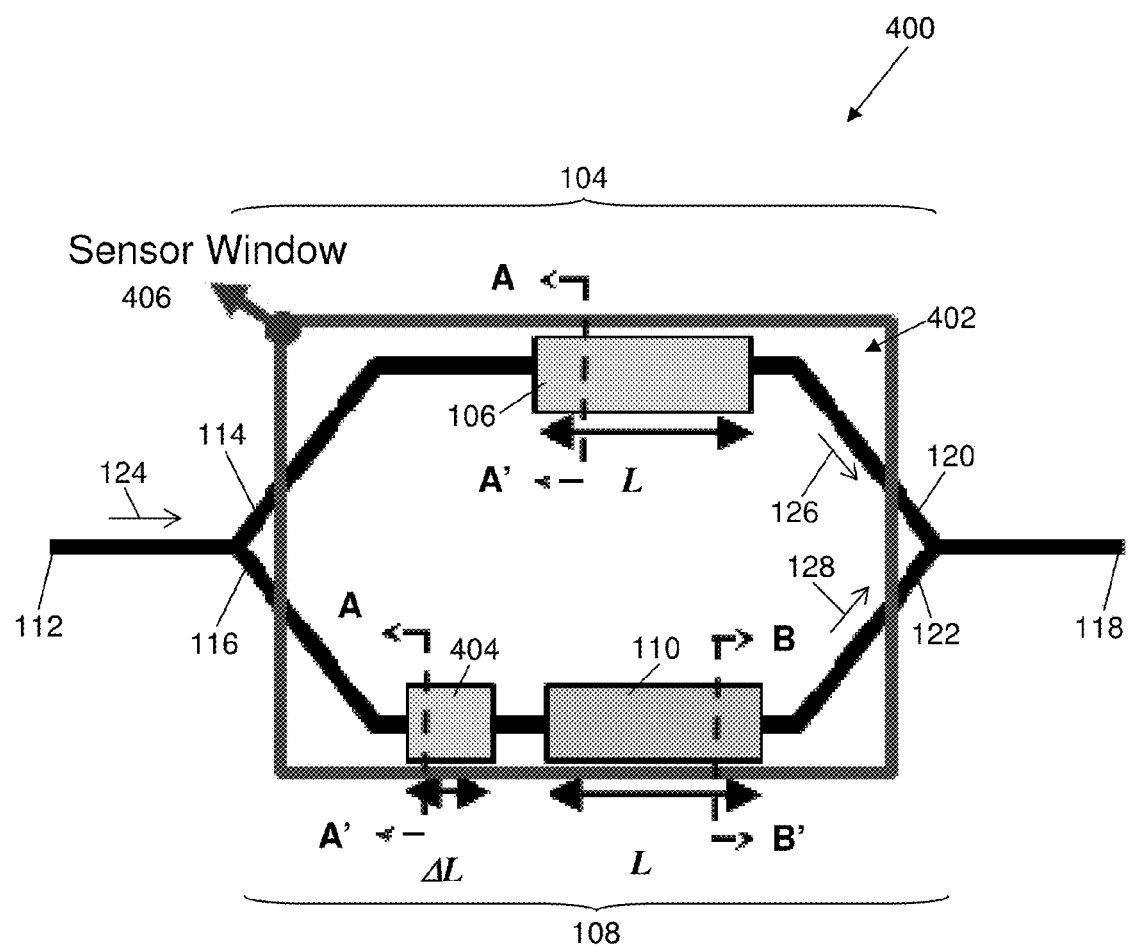
FIG. 4 shows a schematic diagram of an optical circuit for sensing a biological entity in a fluid according to one embodiment.

FIG. 4 shows a schematic diagram of an optical circuit 400 for sensing a biological entity in a fluid according to one embodiment. The sensing arrangement 402 of the optical circuit 400 has a similar configuration as the sensing arrangement 102 of the optical circuit 100, except that the sensing arm 108 further includes a further waveguide 404 coupled in series with the waveguide 110. The further waveguide 404 is coupled between the first end 116 of the sensing arm 108 and the waveguide 110.

In one embodiment, the further waveguide 404 has an identical or a similar structure as the reference waveguide 106. Thus, as shown in FIG. 2, the further waveguide 404 may have a core layer 202 disposed above a first cladding layer 204. The further waveguide 404 may have a second cladding layer 206 disposed above the core layer 202 and the first cladding layer 204. The core layer 202 may include at least one of silicon nitride and silicon (e.g. silicon nitride, silicon or a combination of silicon nitride and silicon). The first cladding layer 204 may have the same materials as the core layer 202. The second cladding layer 206 may include silicon oxide.

The reference arm 104 having the reference waveguide 106 and the sensing arm 108 having the waveguide 110 and the further waveguide 404 are disposed in a sensing window 406 of the optical circuit 400. In other words, the sensing arrangement 402 has a sensing window 406 extending across the reference arm 404 and the sensing arm 408. The components in the sensing window 406 contact e.g. the micro-fluid of the target chemical. The waveguide 110 may be a biosensing waveguide. The further waveguide 404 may be a non-biosensing waveguide.

Lengths of the reference waveguide 106 and the waveguide 110 are configured in accordance with a temperature dependency reduction criterion. Thus, the sensing arrangement 102 may be temperature independent or the temperature dependency of the sensing arrangement 102 may be reduced. The lengths of the reference waveguide 106 and the waveguide 110 are further configured in accordance with refractive indices of the reference waveguide 106 ($n_{\textit{eff}1}$) and the waveguide 110 ($n_{\textit{eff}2}$).

A length of the further waveguide 404 is configured in accordance with the temperature dependency reduction criterion. The length of the further waveguide 404 is further configured in accordance with the refractive index ($n_{\textit{eff}1}$) of the reference waveguide 106, the refractive index ($n_{\textit{eff}2}$) of the waveguide 110 and a refractive index of the further waveguide 404.

In one embodiment, the reference waveguide 106 and the waveguide 110 have the same length (L). The reference waveguide 106 and the further waveguide 404 have the same refractive index. The reference waveguide 106 and the further waveguide 404 have the same cross-sectional area.

In one embodiment, the sensing arrangement 402 may be temperature-independent by proper design including the cross-section dimensions and lengths of the reference arm 104 and the sensing arm 108 (e.g. the cross-section dimensions and lengths of the reference waveguide 106, the waveguide 110 and the further waveguide 404). When the cross-sections of the reference waveguide 106, the waveguide 110 and the further waveguide 404 are fixed, a ratio between the length (ΔL) of the further waveguide 404 and the length (L) between the reference waveguide 106/the waveguide 110 may determines the temperature dependence of the sensing arrangement 402.

Figure 5:
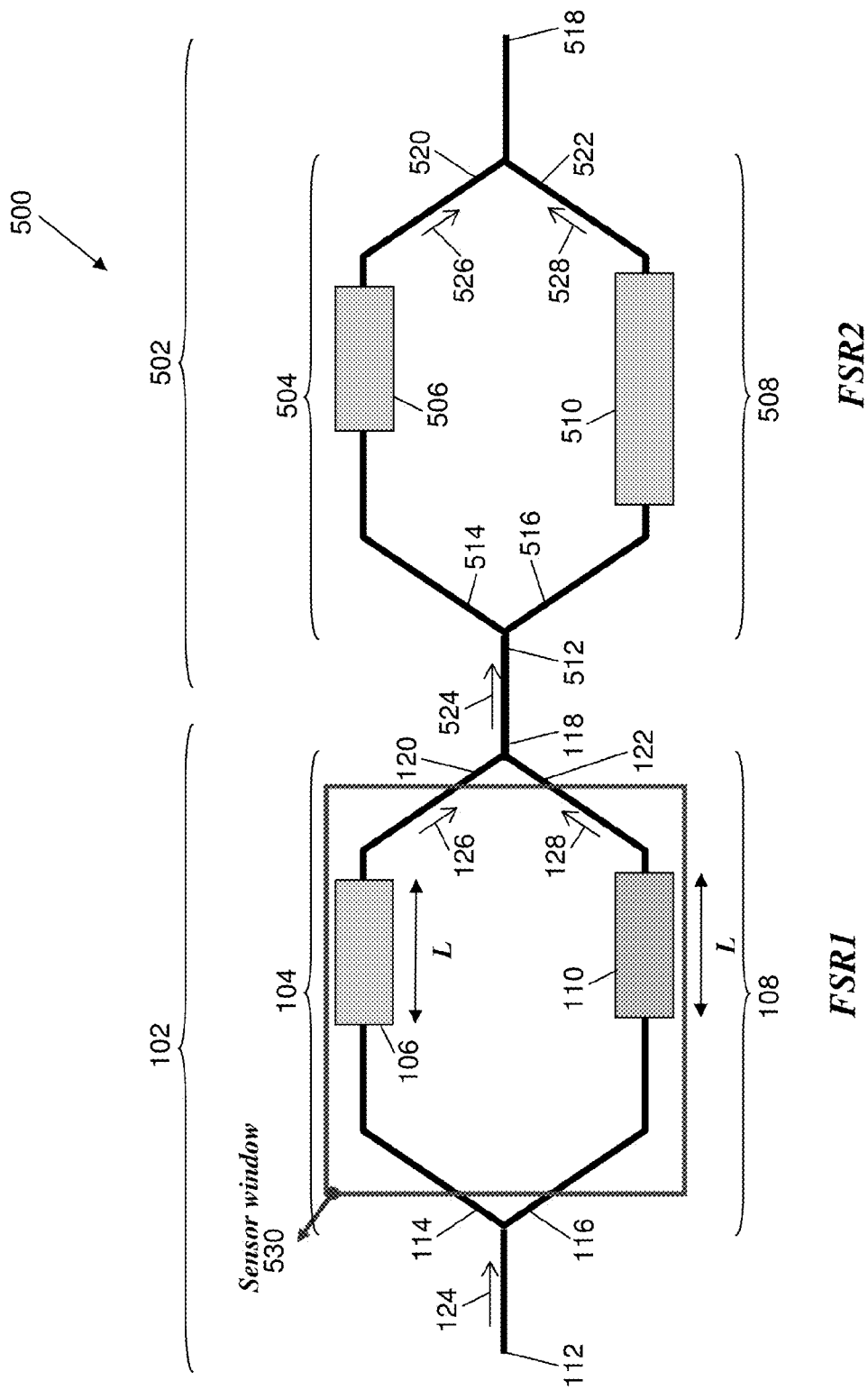
FIG. 5 shows a schematic diagram of an optical circuit for sensing a biological entity in a fluid according to one embodiment.

FIG. 5 shows a schematic diagram of an optical circuit 500 for sensing a biological entity in a fluid according to one embodiment. The optical circuit 500 includes a sensing arrangement 102 as described above and as shown in FIG. 1 and a further sensing arrangement 502. The further sensing arrangement 502 is coupled to the sensing arrangement 102.

The further sensing arrangement 502 has an identical or similar configuration as the sensing arrangement 102. The further sensing arrangement 502 has a reference arm 504 having a reference waveguide 506 and a sensing arm 508 having a waveguide 510. The reference waveguide 506 and the waveguide 510 of the further sensing arrangement 502 have an identical structure or a similar structure as the reference waveguide 106 and the waveguide 110 of the sensing arrangement 102 respectively. The reference waveguide 506 and the waveguide 510 of the further sensing arrangement 502 may respectively have the same structure as shown in and as described with reference to FIGS. 2 and 3. The reference waveguide 506 of the further sensing arrangement 502 and the reference waveguide 106 of the sensing arrangement 102 may have different lengths. The waveguide 510 of the further sensing arrangement 502 and the waveguide 110 of the sensing arrangement 102 may have different lengths.

The further sensing arrangement 502 further includes an input port 512 coupled to a first end 514 of the reference arm 504 and a first end 516 of the sensing arm 508. The input port 512 of the further sensing arrangement 502 is also coupled to the output port 118 of the sensing arrangement 102. The further sensing arrangement 502 includes an output port 518 coupled to a second end 520 of the reference arm 504 and a second end 522 of the sensing arm 508. The input port 512 is configured to receive an optical signal 524 (e.g. a combined signal of the optical signal 126 and the optical signal 128) from the output port 118 of the sensing arrangement 102 and to direct the optical signal 524 to the first end 514 of the reference arm 504 and the first end 516 of the sensing arm 508. The output port 518 is configured to combine an optical signal 526 from the second end 520 of the reference arm 504 and an optical signal 528 from the second end 522 of the sensing arm 508.

In one embodiment, the sensing arrangement 102 may be used as a sensing Mach Zehnder interferometer (MZI). The further sensing arrangement 502 may be used as a reference Mach Zehnder interferometer (MZI). The sensing arrangement 102 may contact e.g. a micro-fluid of a target chemical. The reference arm 104 having the reference waveguide 106 and the sensing arm 108 having the waveguide 110 are disposed in a sensing window 530 of the optical circuit 500. In other words, the sensing arrangement 102 has a sensing window 530 extending across the reference arm 104 and the sensing arm 108. The components in the sensing window 530 contact e.g. the micro-fluid of the target chemical. The further sensing arrangement 502 may be covered with a cladding layer (not shown). In other words, the further sensing arrangement 502 has no sensor window extending across the reference arm 504 and the sensing arm 508. The cladding layer may include silicon oxide. Covering the further sensing arrangement 502 with a cladding layer can prevent the further sensing arrangement 502 from contacting the micro-fluid of the target chemical or analyte. This may increase the sensitivity of the optical circuit 600. Covering the further sensing arrangement 502 with a cladding layer can also maintain thermal independence.

In one embodiment, the sensing arrangement 102 may have a free spectral range FSR1. The further sensing arrangement 502 may have a free spectral range FSR2. The sensing arrangement 102 and the further sensing arrangement 502 have different free spectral range.

In one embodiment, the optical circuit 500 may be an athermal biosensor which uses a two-MZI cascade with different free spectral range (FSR). The sensor window 503 is open only on one of the two MZI. The optical circuit 500 can utilize Vernier effect to increase the sensitivity of e.g. a biosensor while keeping the temperature independence.

Figure 6:
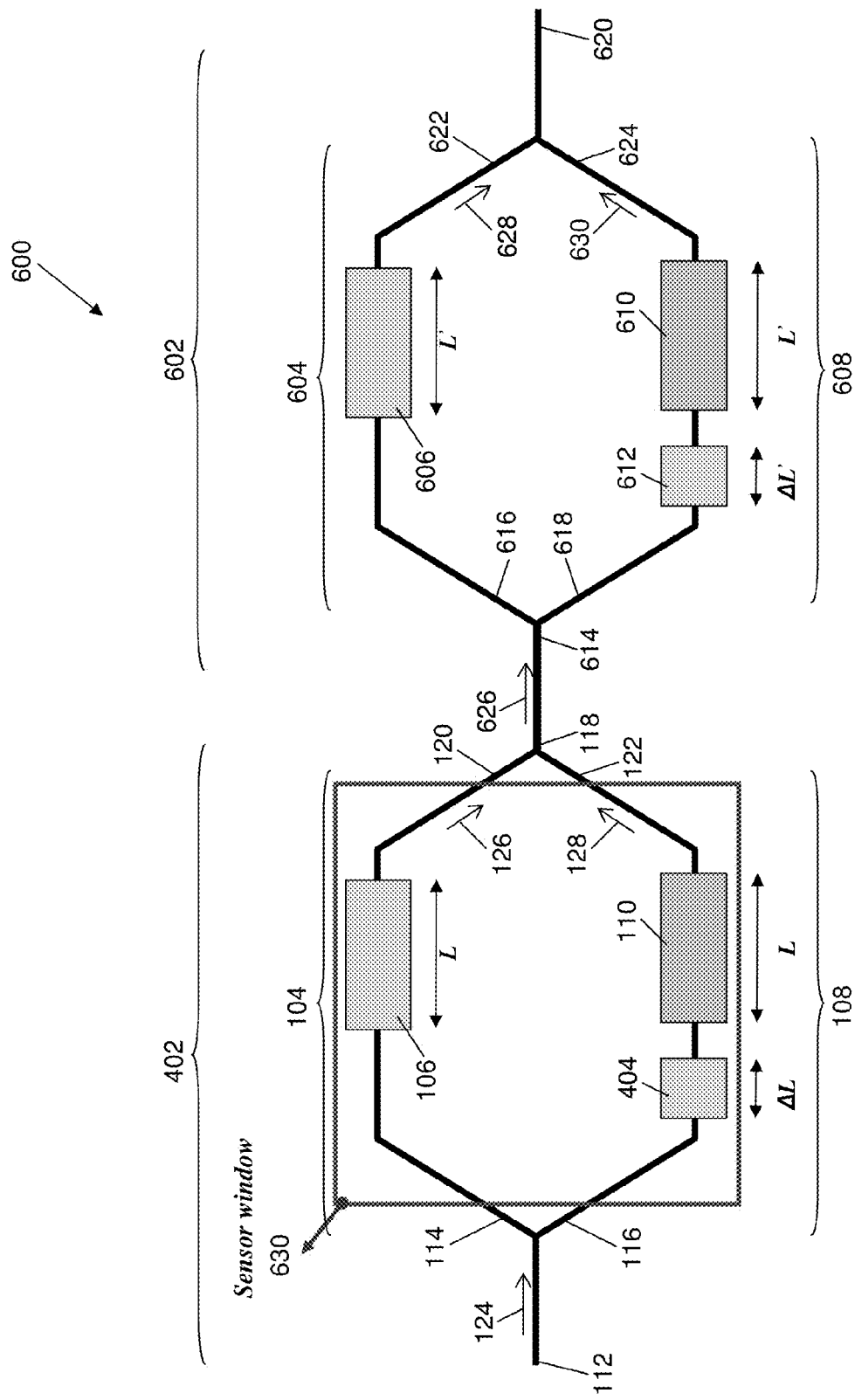
FIG. 6 shows a schematic diagram of an optical circuit for sensing a biological entity in a fluid according to one embodiment.

FIG. 6 shows a schematic diagram of an optical circuit 600 for sensing a biological entity in a fluid according to one embodiment. The optical circuit 600 includes a sensing arrangement 402 as described above and as shown in FIG. 4 and a further sensing arrangement 602. The further sensing arrangement 602 is coupled to the sensing arrangement 402.

The further sensing arrangement 602 has an identical or similar configuration as the sensing arrangement 402. The further sensing arrangement 602 has a reference arm 604 having a reference waveguide 606 and a sensing arm 608 having a waveguide 610 and a further waveguide 612. The reference waveguide 606, the waveguide 610 and the further waveguide 612 of the further sensing arrangement 602 have an identical or similar structure as the reference waveguide 106, the waveguide 110 and the further waveguide 404 of the sensing arrangement 402 respectively. The reference waveguide 606 and the further waveguide 612 may have the same structure as shown in and as described with reference to FIG. 2. The waveguide 610 of the further sensing arrangement 602 may have the same structure as shown in and as described with reference to FIG. 3. The reference waveguide 606 of the further sensing arrangement 602 and the reference waveguide 106 of the sensing arrangement 402 may have different lengths. The waveguide 610 of the further sensing arrangement 502 and the waveguide 110 of the sensing arrangement 402 may have different lengths. The further waveguide 612 of the further sensing arrangement 602 and the further waveguide 404 of the sensing arrangement 402 may have different lengths.

The further sensing arrangement 602 further includes an input port 614 coupled to a first end 616 of the reference arm 604 and a first end 618 of the sensing arm 608. The input port 614 of the further sensing arrangement 602 is also coupled to the output port 118 of the sensing arrangement 402. The further sensing arrangement 602 includes an output port 620 coupled to a second end 622 of the reference arm 604 and a second end 624 of the sensing arm 608. The input port 614 is configured to receive an optical signal 626 (e.g. a combined signal of the optical signal 126 and the optical signal 128) from the output port 118 of the sensing arrangement 402 and to direct the optical signal 626 to the first end 616 of the reference arm 604 and the first end 618 of the sensing arm 608. The output port 620 is configured to combine an optical signal 628 from the second end 622 of the reference arm 604 and an optical signal 630 from the second end 624 of the sensing arm 608.

In one embodiment, the sensing arrangement 402 may be used as a sensing Mach Zehnder interferometer (MZI). The further sensing arrangement 602 may be used as a reference Mach Zehnder interferometer (MZI). The sensing arrangement 402 may contact e.g. a micro-fluid of a target chemical. The reference arm 104 having the reference waveguide 106 and the sensing arm 108 having the waveguide 110 and the further waveguide 404 are disposed in a sensing window 630 of the optical circuit 600. In other words, the sensing arrangement 402 has a sensing window 630 extending across the reference arm 104 and the sensing arm 108. The components in the sensing window 630 contact e.g. the micro-fluid of the target chemical. The further sensing arrangement 602 may be covered with a cladding layer (not shown). In other words, the further sensing arrangement 602 has no sensor window extending across the reference arm 604 and the sensing arm 608. The cladding layer may include silicon oxide. Covering the further sensing arrangement 602 with a cladding layer can prevent the further sensing arrangement 602 from contacting the micro-fluid of the target chemical or analyte. This may increase the sensitivity of the optical circuit 600. Covering the further sensing arrangement 602 with a cladding layer can also maintain thermal independence.

In one embodiment, the sensing arrangement 102 may have a free spectral range FSR1. The further sensing arrangement 502 may have a free spectral range FSR2. The sensing arrangement 102 and the further sensing arrangement 502 have different free spectral range.

In one embodiment, the optical circuit 600 may be an athermal biosensor which uses a two-MZI cascade with different free spectral range (FSR). The sensor window 603 is open only on one of the two MZI. The optical circuit 600 can utilize Vernier effect to increase the sensitivity of e.g. a biosensor while keeping the temperature independence.

A method of configuring an optical circuit for sensing a biological entity in a fluid is described. The optical circuit includes a sensing arrangement including a reference arm having a reference waveguide and a sensing arm having a waveguide. In one embodiment, the method includes determining lengths of the reference waveguide and the waveguide based on a temperature dependency reduction criterion.

The temperature dependency reduction criterion may be a temperature dependency minimizing criterion. The temperature dependency minimizing criterion may be to minimize the temperature dependency of the optical circuit. The temperature dependency of the optical circuit may be minimized to zero.

In one embodiment, the method may further include determining the lengths of the reference waveguide and the waveguide based on refractive indices of the reference waveguide and the waveguide.

In one embodiment, the sensing arm of the sensing arrangement of the optical circuit may further include a further waveguide coupled in series with the waveguide. The method may further include determining a length of the further waveguide based on a temperature dependency reduction criterion. The method may further include determining the length of the further waveguide based on the refractive index of the reference waveguide, the refractive index of the waveguide and a refractive index of the further waveguide.

In one embodiment, the optical circuit may further include a further sensing arrangement coupled to the sensing arrangement. The method may further include determining lengths and cross-sectional areas of a reference arm and a sensing arm of the further sensing arrangement based on a temperature dependency reduction criterion, and determining the lengths and the cross-sectional areas of the reference arm and the sensing arm of the further sensing arrangement based on Vernier effect.

Determining the lengths and the cross-sectional areas of the reference arm and the sensing arm of the further sensing arrangement based on Vernier effect may include determining the lengths and the cross-sectional areas of the reference arm and the sensing arm of the further sensing arrangement based on a free spectral range of the sensing arrangement and a free spectral range of the further sensing arrangement. The length and the cross-sectional area of the reference arm of the further sensing arrangement may include a length and a cross-sectional area of a reference waveguide of the reference arm of the further sensing arrangement. The length and the cross-sectional area of the sensing arm of the further sensing arrangement may include a length and a cross-sectional area of a waveguide of the sensing arm of the further sensing arrangement. The length and the cross-sectional area of the sensing arm of the further sensing arrangement may further include a length and a cross-sectional area of a further waveguide of the sensing arm of the further sensing arrangement.

Details of configuring an optical circuit for sensing a biological entity in a fluid is described in the following.

A transmitting wavelength λ of a sensing arrangement of an optical circuit is given as:

$$m\lambda = n_{eff1}\Delta L + (n_{eff2} - n_{eff1})L \quad (1)$$

where $n_{eff1}$ is effective refractive index of a reference waveguide and of a further waveguide, $n_{eff2}$ is effective refractive index of a waveguide, m is an integer for constructive interference or a half-integer for destructive interference, L is a length of the reference waveguide and of the waveguide, and ΔL is a length of the further waveguide.

Considering the wavelength-dispersion effect, equation (1) changes to $$M = m - \Delta L \frac{\partial n_{eff1}}{\partial \lambda} - L\frac{\partial (n_{eff2} - n_{eff1})}{\partial \lambda} \quad (2)$$

where M is an interference order under the wavelength λ.

The temperature sensitivity of the transmitting wavelength λ can be expressed as $$\frac{\partial \lambda}{\partial T} = \frac{\Delta L}{M}\frac{\partial n_{eff1}}{\partial T} + \frac{L}{M}\frac{\partial (n_{eff2} - n_{eff1})}{\partial T} \quad (3)$$

where T is the temperature.

Thermal independent is satisfied when ∂λ/∂T=0. When ∂λ/∂T=0, $$\frac{\Delta L}{L} = \frac{\frac{\partial (n_{eff1} - n_{eff2})}{\partial T}}{\frac{\partial n_{eff1}}{\partial T}} \quad (4)$$

The above equations (1) to (4) can be applied for the optical circuit 400 and the optical circuit 600. As the optical circuit 100 and the optical circuit 500 do not have a further waveguide in the sensing arm, the above equations (1) to (4) are different for the optical circuit 100 and the optical circuit 500. Thus, the temperature sensitivity of the transmitting wavelength λ for the optical circuit 100, 500 can be expressed as $$\frac{\partial \lambda}{\partial T} = \frac{L}{M} \frac{\partial (n_{eff2} - n_{eff1})}{\partial T}$$

when $\partial \lambda / \partial T = 0$, $$\frac{\partial (n_{eff2} - n_{eff1})}{\partial T} = 0$$

A sensitivity of an optical circuit having a sensing arrangement can be expressed as $$S_{sensor} = \frac{\partial \lambda_{res}}{\partial n_{tar}} = \frac{\partial n_{eff}}{\partial n_{tar}} \frac{\lambda}{n_g} \quad (5)$$

where $\lambda$, is a transmitting wavelength of the sensing arrangement, $\lambda_{res}$ is a resonance wavelength, $n_{tar}$ is a refractive index of target biochemical under testing, $n_{eff}$ is an effective index of the sensing waveguide, and $n_g$ is a group index of the sensing waveguide.

A sensitivity of an optical circuit having a further sensing arrangement coupled to a sensing arrangement (e.g. a cascade arrangement of the sensing arrangement and the further sensing arrangement) can be expressed as $$S_{cascade} = M \cdot S_{sensor} = \frac{FSR_2}{FSR_2 - FSR_1} \cdot S_{sensor} \quad (6)$$

where M is a sensitivity enhancement factor, $FSR_1$ is a free spectral range of the sensing arrangement, and $FSR_2$ is a free spectral range of the further sensing arrangement.
From equation (6), it can be understood that $$M = \frac{FSR_2}{FSR_2 - FSR_1} \quad (7)$$

The above equations (5) to (7) can be applied for the optical circuits 100, 400, 500, 600.

The sensitivity of the optical circuit (e.g. athermal biosensor) can be improved by cascading two sensing arrangements (e.g. the sensing arrangement and the further sensing arrangement) together. Compared to the sensitivity of the optical circuit 400 (e.g. a single ring resonator sensor) as shown in equation (5), the sensitivity of the optical circuit 600 (e.g. cascaded ring resonators sensor) is enhanced with a factor of $FSR_1/(FSR_1-FSR_2)$ as shown in equation (6). Vernier effect is utilized in two cascaded Mach Zehnder interferometers (MZIs). Thus, the sensitivity of the optical circuit can be increased while keeping its thermal independence.

In one embodiment, the refractive index of silicon nitride ($n_{SiN}$) is about 2.0. The refractive index of oxide ($n_{oxide}$) is about 1.46. The thermal optical coefficient of silicon nitride ($\partial n_{SiN}/\partial T$) is about $4.0 \times 10^{-5}$. The thermal optical coefficient of oxide ($\partial n_{oxide}/\partial T$) is about $1.0 \times 10^{-5}$.

Thermal optical coefficients ($\partial n/\partial T$) of the reference waveguide 106 and the waveguide 110 can be achieved through experiment.

Figure 7:
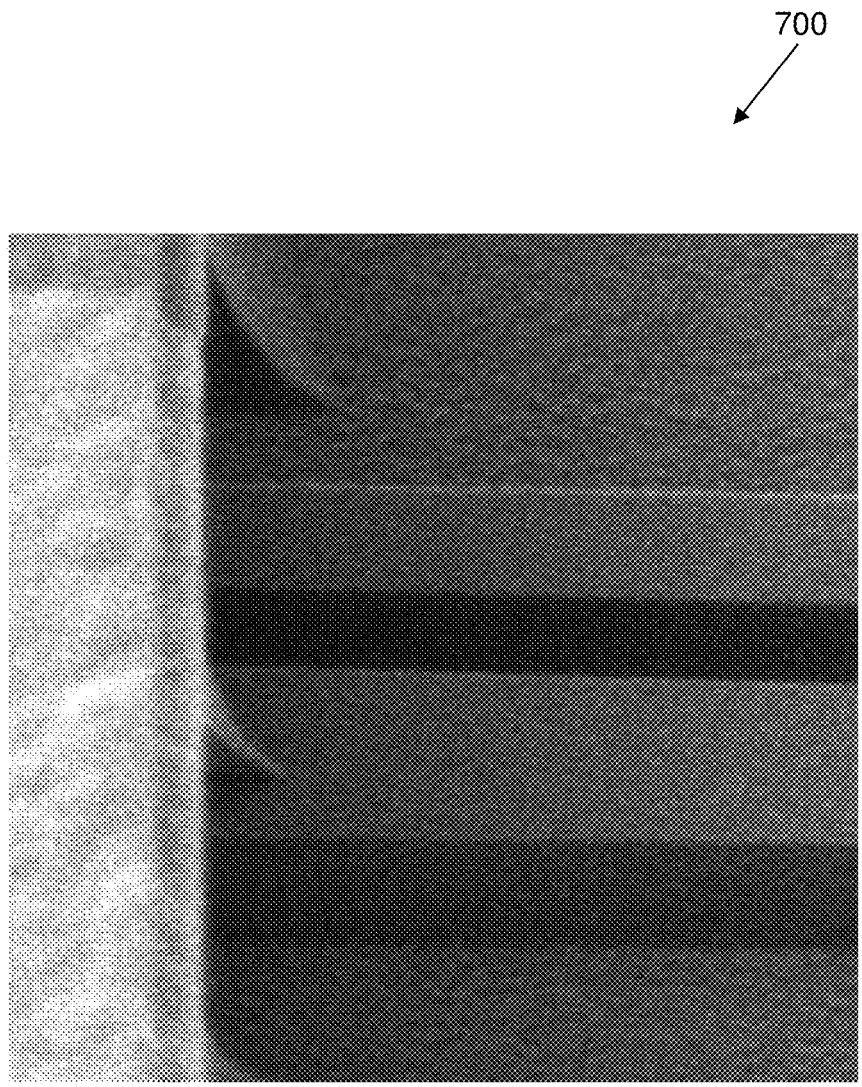
FIG. 7 shows scanning electron microscope (SEM) pictures of a waveguide of an optical circuit according to one embodiment.

Experiments can be conducted for the waveguide 110 with oxide cladding, air cladding and cladding of sodium chloride (NaCl) under different temperatures. A Peltier heat pump may be used for the thermal test. FIG. 7 shows scanning electron microscope (SEM) pictures of the waveguide 110 in a form of a silicon nitride slot waveguide 700 with air cladding. The silicon nitride slot waveguide 700 shows good profile under SEM.

Figure 8A:
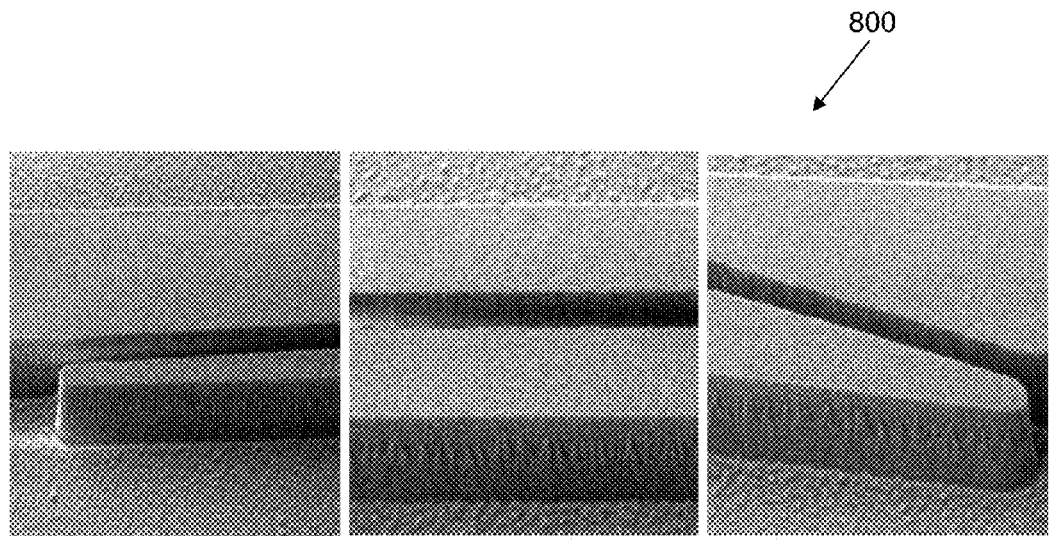
FIG. 8a shows SEM pictures of a waveguide of an optical circuit according to one embodiment.
Figure 8B:
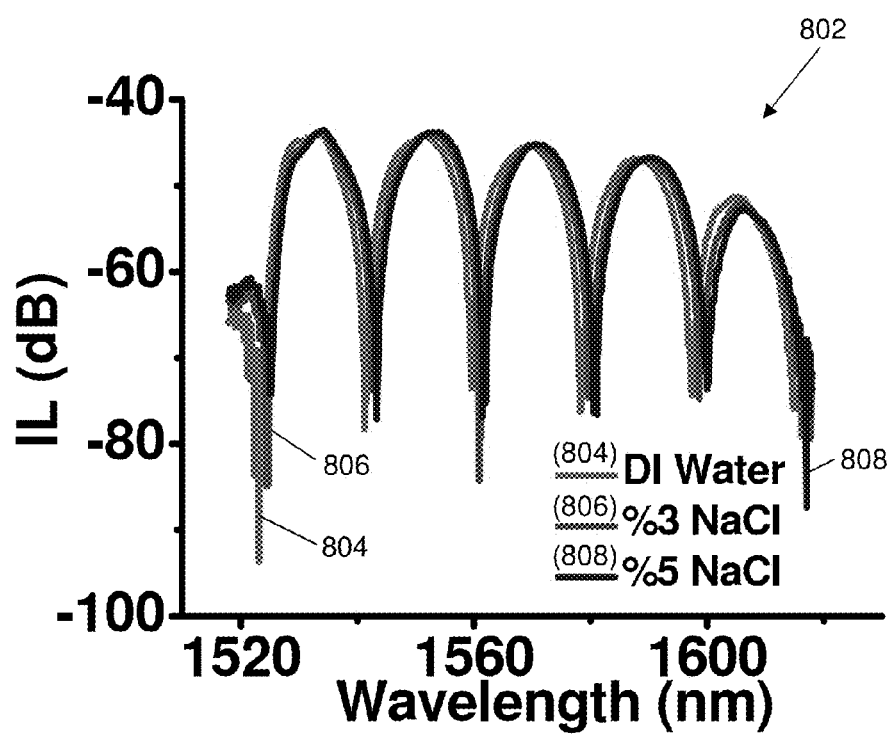
FIG. 8b shows a graph of experimental results of a waveguide of an optical circuit according to one embodiment.

FIG. 8a shows SEM pictures of the waveguide 110 in a form of a silicon nitride slot waveguide Mach Zehnder interferometer (MZI) 800 with air cladding. A similar experiment is also carried for the silicon nitride slot waveguide MZI 800. FIG. 8b shows a graph 802 of experimental results (e.g. of a spectrum testing) for the silicon nitride slot waveguide MZI 800 with cladding of NaCl solution with different concentrations. Graph 802 shows insertion loss (IL) of the silicon nitride slot waveguide MZI 800 plotted against wavelength of an optical signal. Graph 802 shows a plot 804 of experimental results for a cladding of deionized water. Graph 802 shows a plot 806 of experimental results for a cladding of NaCl solution with 3% concentration level. Graph 802 shows a plot 808 of experimental results for a cladding of NaCl solution with 5% concentration level.

A biosensor testing may be carried out for the silicon nitride slot waveguide MZI 800. A measured refractive index sensitivity of the silicon nitride slot waveguide MZI 800 may be about 268 nm/RIU. A detection limit of the silicon nitride slot waveguide MZI 800 may reach $2.2 \times 10^{-5}$ with a detection minimum value of 2 pm.

Figure 9:
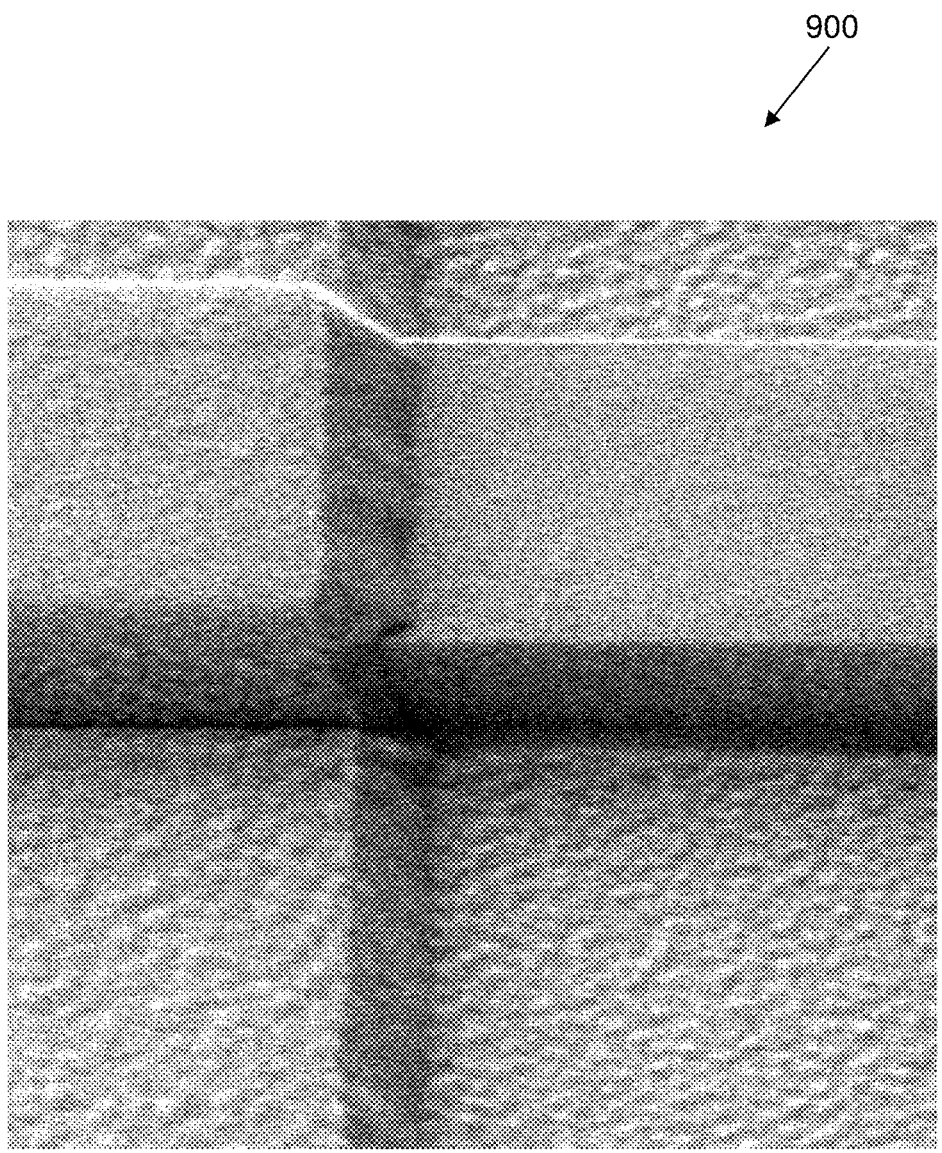
FIG. 9 shows SEM pictures of a reference waveguide of an optical circuit according to one embodiment.

FIG. 9 shows scanning electron microscope (SEM) pictures of the waveguide 106 in a form of a silicon nitride strip waveguide 900 with air cladding. The silicon nitride strip waveguide 900 shows good profile under SEM.

Figure 10:
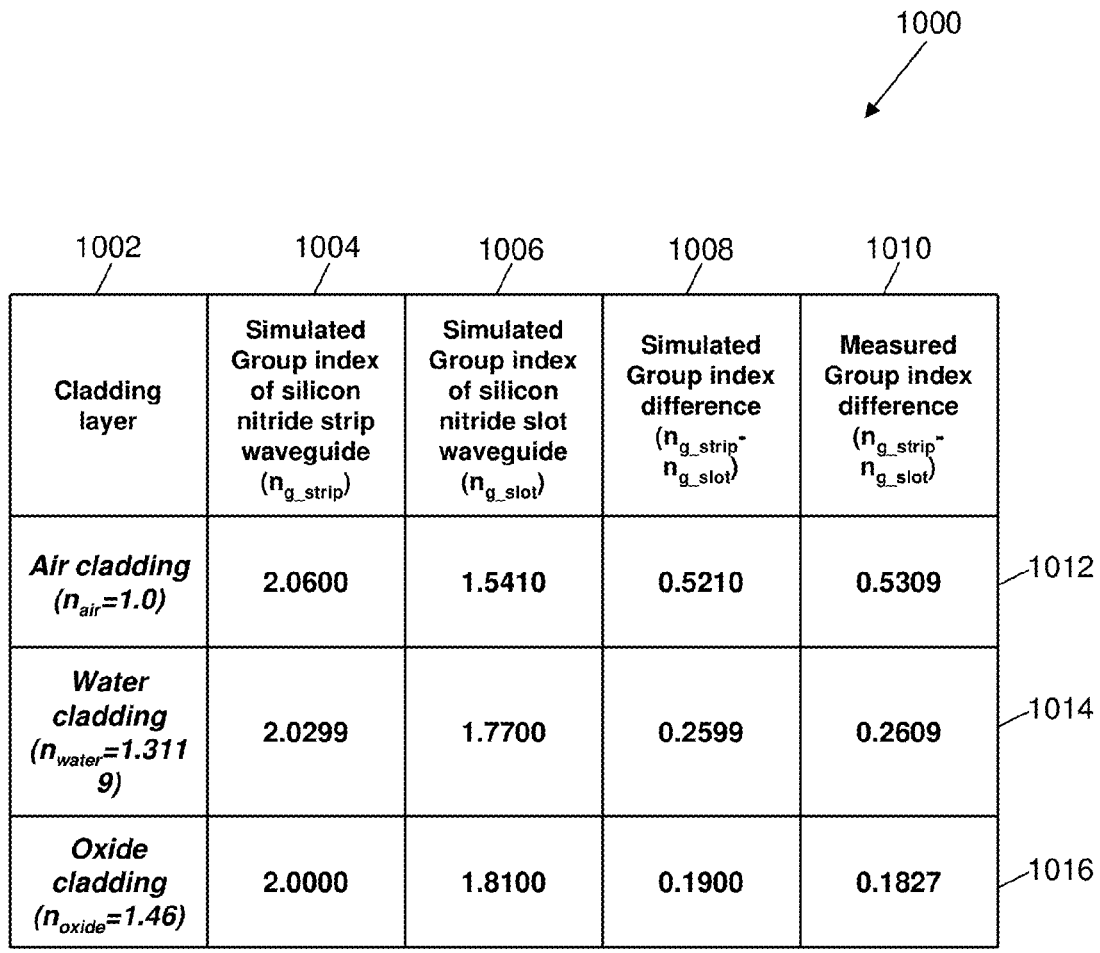
FIG. 10 shows a table listing simulated group index and measured group index of a reference waveguide and a waveguide of an optical circuit according to one embodiment.

FIG. 10 shows a table 1000 listing simulated group index and measured group index of the reference waveguide 106 and the waveguide 110 with different claddings. Column 1002 shows the cladding layer used, column 1004 shows a simulated group index of the reference waveguide 106 (e.g. silicon nitride strip waveguide), column 1006 shows a simulated group index of the waveguide 110 (e.g. silicon nitride slot waveguide), column 1008 shows a simulated group index difference between the reference waveguide 106 and the waveguide 110, and column 1010 shows a measured group index difference between the reference waveguide 106 and the waveguide 110.

Row 1012 shows that with an air cladding having a refractive index of 1.0, the simulated group index of the reference waveguide 106 is about 2.06, the simulated group index of the waveguide 110 is about 1.541, the simulated group index difference is about 0.521 and the measured group index difference is about 0.5309. Row 1014 shows that with a water cladding having a refractive index of 1.3119, the simulated group index of the reference waveguide 106 is about 2.0299, the simulated group index of the waveguide 110 is about 1.77, the simulated group index difference is about 0.2599 and the measured group index difference is about 0.2609. Row 1016 shows that with an oxide cladding having a refractive index of 1.46, the simulated group index of the reference waveguide 106 is about 2.0, the simulated group index of the waveguide 110 is about 1.81, the simulated group index difference is about 0.19 and the measured group index difference is about 0.1827. It can be observed from table 1000 that the simulated group index difference is close to the measured group index difference.

FIG. 11 shows a table 1100 listing the main parameters of an optical circuit (e.g. optical circuit 400) in water cladding. Column 1102 shows a width of the reference waveguide 106 (e.g. silicon nitride strip waveguide), column 1104 shows a simulated group index of the reference waveguide 106, column 1106 shows a simulated thermal optic coefficient of the reference waveguide 106, column 1108 shows a simulated group index of the waveguide 110 (e.g. silicon nitride slot waveguide), column 1110 shows a simulated thermal optic coefficient of the waveguide 110, and column 1112 shows the length ($\Delta L$) of the further waveguide 404 when the length (L) of the reference waveguide 106/waveguide 110 is 1 mm.

In one embodiment, the waveguide 110 has a simulated group index of 1.77 and a simulated thermal optic coefficient of $2.0 \times 10^{-5}$.

Row 1114 shows that the reference waveguide 106 has a width of 1.0 μm, a simulated group index of 2.0276, and a simulated thermal optic coefficient of $3.4 \times 10^{-5}$. Row 1114 also shows that the length ($\Delta L$) of the further waveguide 404 is 411.765 μm when the length (L) of the reference waveguide 106/waveguide 110 is 1 mm.

Row 1116 shows that the reference waveguide 106 has a width of 0.7 μm, a simulated group index of 1.9754, and a simulated thermal optic coefficient of $2.9 \times 10^{-5}$. Row 1116 also shows that the length ($\Delta L$) of the further waveguide 404 is 310.345 μm when the length (L) of the reference waveguide 106/waveguide 110 is 1 mm.

Row 1118 shows that the reference waveguide 106 has a width of 0.55 μm, a simulated group index of 1.8845, and a simulated thermal optic coefficient of $2.45 \times 10^{-5}$. Row 1118 also shows that the length ($\Delta L$) of the further waveguide 404 is 183.673 μm when the length (L) of the reference waveguide 106/waveguide 110 is 1 mm.

Row 1120 shows that the reference waveguide 106 has a width of 0.5 μm, a simulated group index of 1.838, and a simulated thermal optic coefficient of $2.3 \times 10^{-5}$. Row 1120 also shows that the length ($\Delta L$) of the further waveguide 404 is 130.435 μm when the length (L) of the reference waveguide 106/waveguide 110 is 1 mm.

FIG. 12 shows a table 1200 listing the main parameters of an optical circuit having a sensing arrangement and a further arrangement arranged in a cascade (e.g. optical circuit 600). In one embodiment, the sensing arrangement 402 is a sensing MZI and the further sensing arrangement 602 is a reference MZI. The sensing arrangement 402 is covered with water cladding and the further sensing arrangement 602 is covered with oxide cladding.

As shown in table 1200, the width of the reference waveguide 106 is 1.0 μm. The length ($L_{sen}$) of the reference waveguide 106 and of the waveguide 110 of the sensing arrangement 402 is 7 mm. With $L_{sen}$=7 mm, the free spectral range ($FSR_1$) of the sensing arrangement 402 is 0.54 nm, and the length ($\Delta L_{sen}$) of the further waveguide 404 is 2,882.355 μm.

When the free spectral range ($FSR_2$) of the further sensing arrangement 602 is 0.52 nm, the length ($L_{ref}$) of the reference waveguide 606 and of the waveguide 610 of the further sensing arrangement 602 is 25.2884 mm. When the free spectral range ($FSR_2$) of the further sensing arrangement 602 is 0.54 nm, the length ($L_{ref}$) of the reference waveguide 606 and of the waveguide 610 of the further sensing arrangement 602 is 24.3518 mm. When the free spectral range ($FSR_2$) of the further sensing arrangement 602 is 0.56 nm, the length ($L_{ref}$) of the reference waveguide 606 and of the waveguide 610 of the further sensing arrangement 602 is 23.4821 mm.

Figure 13:
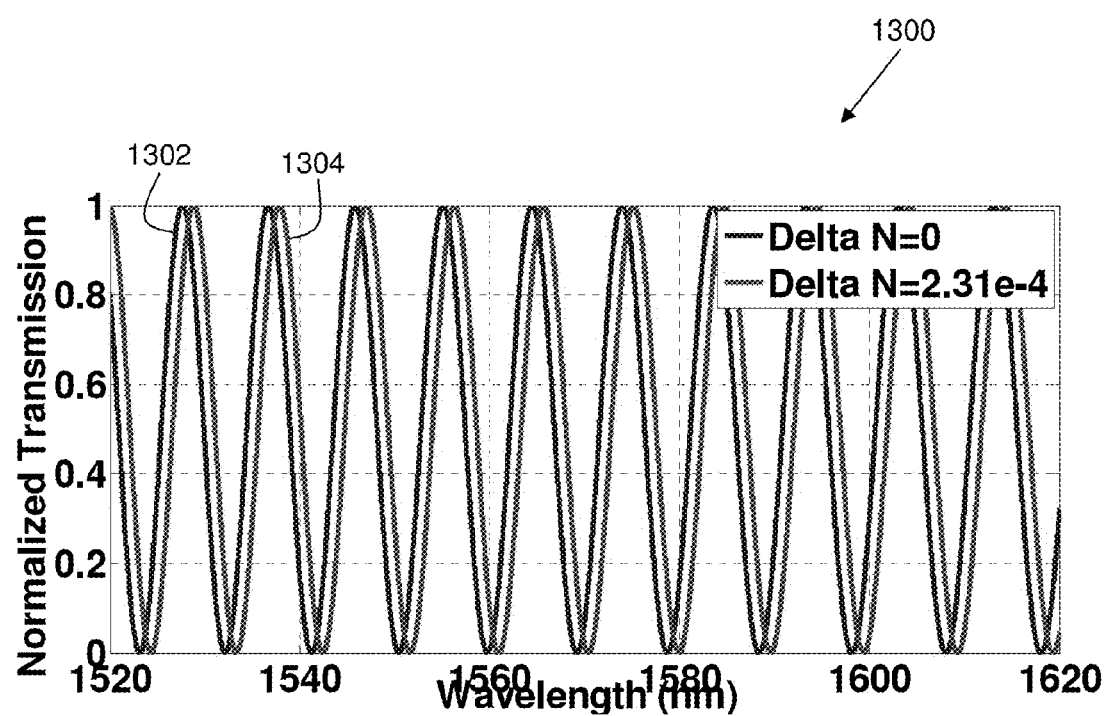
FIG. 13 shows a graph of a simulated output spectrum of a waveguide of an optical circuit according to one embodiment.

FIG. 13 shows a graph 1300 of a simulated output spectrum of the waveguide 110 in a form of a silicon nitride slot waveguide Mach Zehnder interferometer (MZI) 800 of FIG. 8a. Graph 1300 shows a plot 1302 of normalized transmission of an optical signal in the silicon nitride slot waveguide MZI 800 plotted against a wavelength of the optical signal for Delta N ($\Delta N$)=0. Graph 1300 shows a plot 1304 of normalized transmission of the optical signal in the silicon nitride slot waveguide MZI 800 plotted against a wavelength of the optical signal for Delta N ($\Delta N$)=$2.31 \times 10^{-4}$. Delta N ($\Delta N$) represents a change of a refractive index corresponding to target biochemical's concentration variation. The simulated sensitivity of the silicon nitride slot waveguide MZI 800 is about 272 nm/RIU which is close to the measured simulated sensitivity of about 268 nm/RIU.

Figure 14:
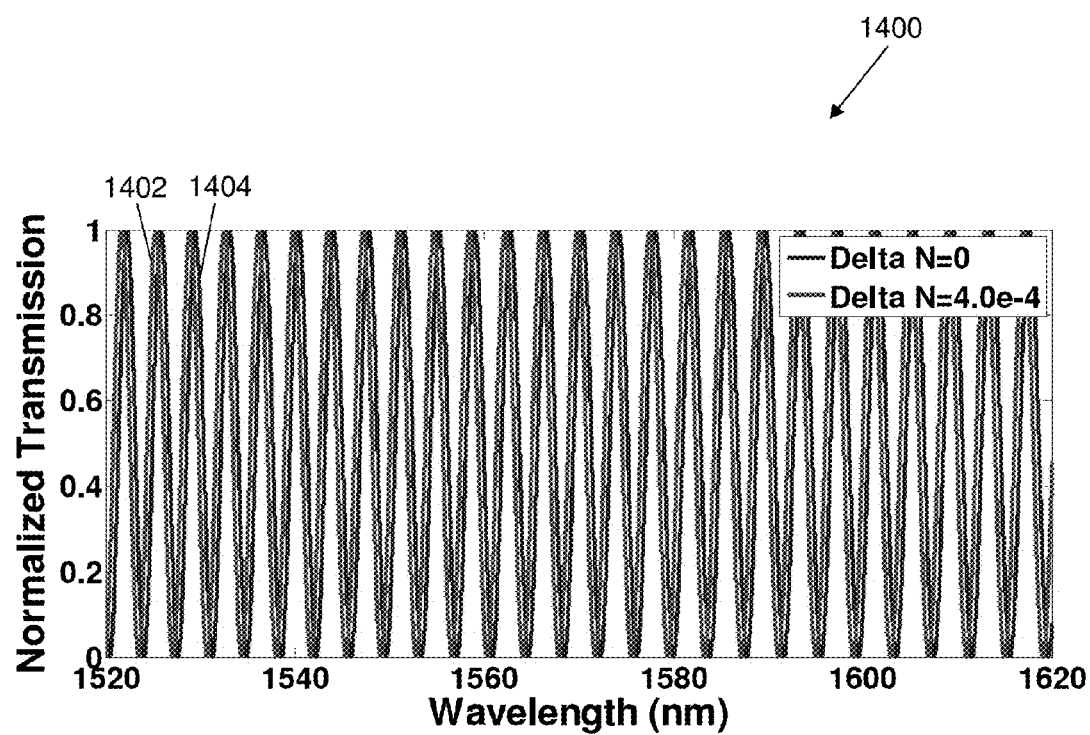
FIG. 14 shows a graph of a simulated output spectrum of an optical circuit according to one embodiment.

FIG. 14 shows a graph 1400 of a simulated output spectrum of an optical circuit having a sensing arrangement (e.g. optical circuit 400). Graph 1400 shows a plot 1402 of normalized transmission of an optical signal in the optical circuit plotted against a wavelength of the optical signal for Delta N ($\Delta N$)=0. Graph 1400 shows a plot 1404 of normalized transmission of the optical signal in the optical circuit plotted against a wavelength of the optical signal for Delta N ($\Delta N$)=$4.0 \times 10^{-4}$. The simulated sensitivity of the optical circuit is about 67.5 nm/RIU.

Figure 15:
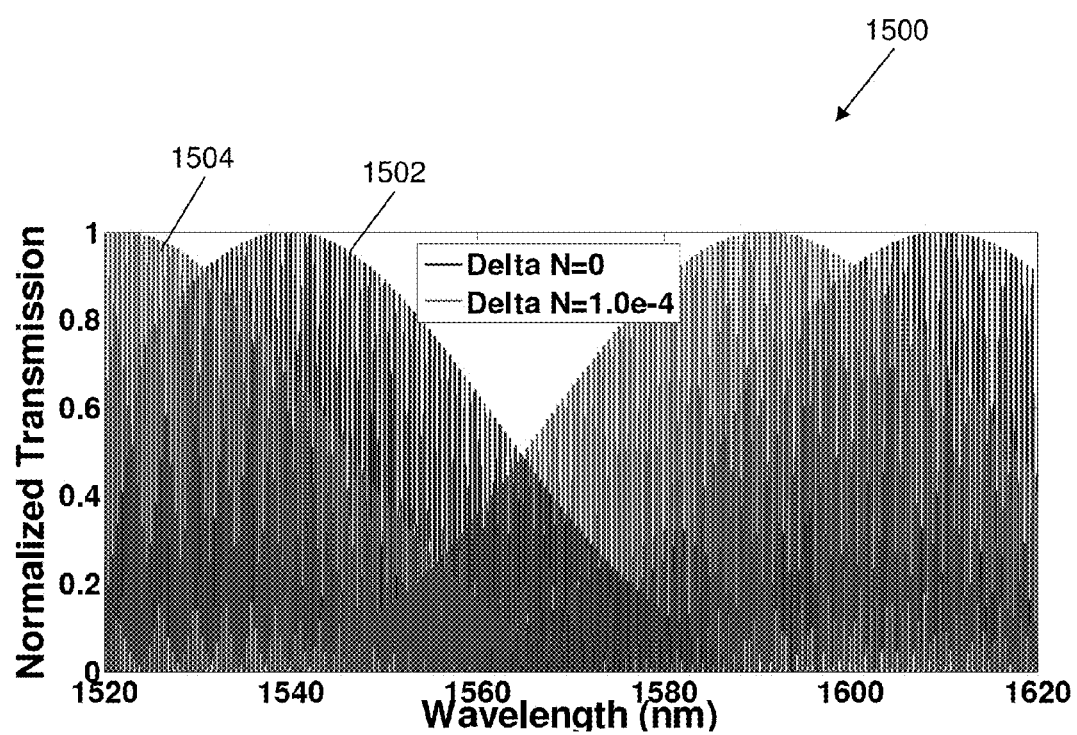
FIG. 15 shows a graph of a simulated output spectrum of an optical circuit according to one embodiment.

FIG. 15 shows a graph 1500 of a simulated output spectrum of an optical circuit having a sensing arrangement and a further sensing arrangement in a cascade configuration (e.g. optical circuit 600). In one embodiment, the sensing arrangement 402 is a sensing MZI and the further sensing arrangement 602 is a reference MZI. Graph 1500 shows a plot 1502 of normalized transmission of an optical signal in the optical circuit plotted against a wavelength of the optical signal for Delta N ($\Delta N$)=0. Graph 1500 shows a plot 1504 of normalized transmission of the optical signal in the optical circuit plotted against a wavelength of the optical signal for Delta N ($\Delta N$)=$1.0 \times 10^{-4}$. The simulated sensitivity of the optical circuit is about 9000 nm/RIU.

Comparing graph 1400 of FIG. 14 and graph 1500 of FIG. 15, the simulated sensitivity of the optical circuit can be increased from 67.5 nm/RIU to 9,000 nm/RIU by having a cascade arrangement of two sensing arrangements. The Vernier effect in cascaded sensing arrangements can increase the sensitivity of the optical circuit.

Given the Vernier effect, if two sensing arrangements (e.g. resonators) are cascaded, when the free spectral range difference between the two sensing arrangements is small compared to the full-width at half-maximum of the resonance peaks of the individual sensing arrangements, a change of the refractive index in the evanescent field of the sensing MZI of the cascaded sensing arrangements will cause a shift of the resonance peaks in its transmission spectrum. The shift of the resonance peaks in its transmission spectrum of the sensing MZI can be translated in a much larger shift of the central wavelength of the envelope peak in the transmission spectrum of the cascaded sensing arrangements as shown in FIG. 15.

Figure 16:
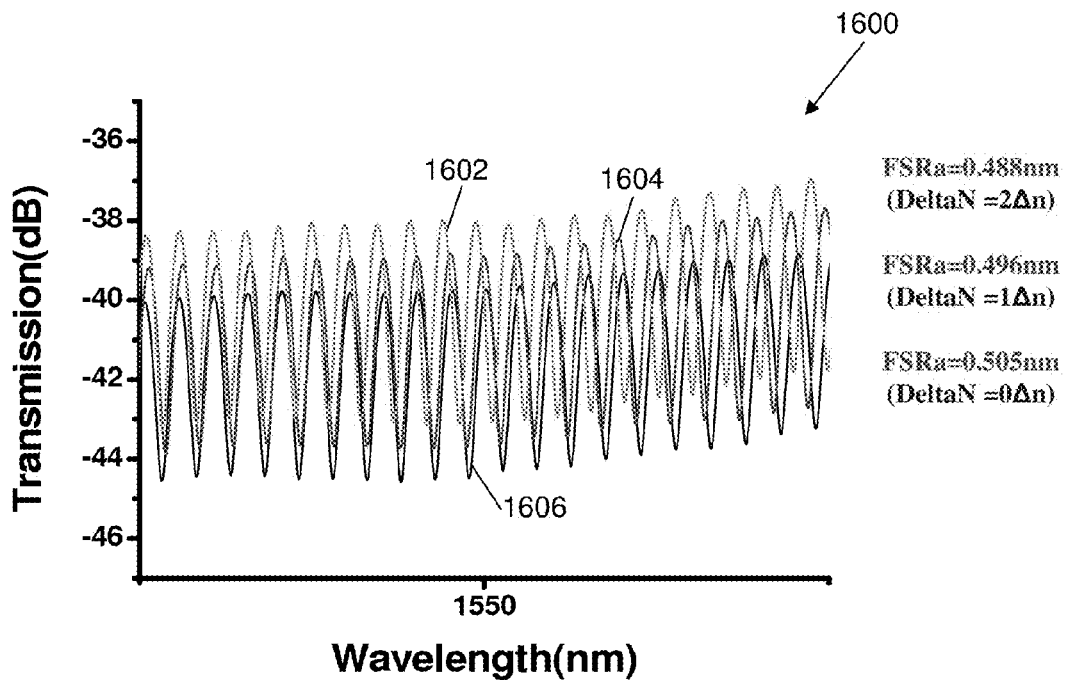
FIG. 16 shows a graph of transmission power of an optical circuit plotted against a wavelength of an optical signal according to one embodiment.

FIG. 16 shows a graph 1600 of transmission power of an optical circuit (e.g. optical circuit 400) plotted against a wavelength of an optical signal. In one embodiment, DeltaN=mΔn, where m=0, 1, 2, . . . , m. Graph 600 shows a plot 1602 for the optical circuit having a free spectral range (FSR) of 0.488 nm and DeltaN of 2Δn. Graph 600 shows a plot 1604 for the optical circuit having a free spectral range (FSR) of 0.496 nm and DeltaN of 1Δn. Graph 600 shows a plot 1606 for the optical circuit having a free spectral range (FSR) of 0.505 nm and DeltaN of 0Δn.

Figure 17:
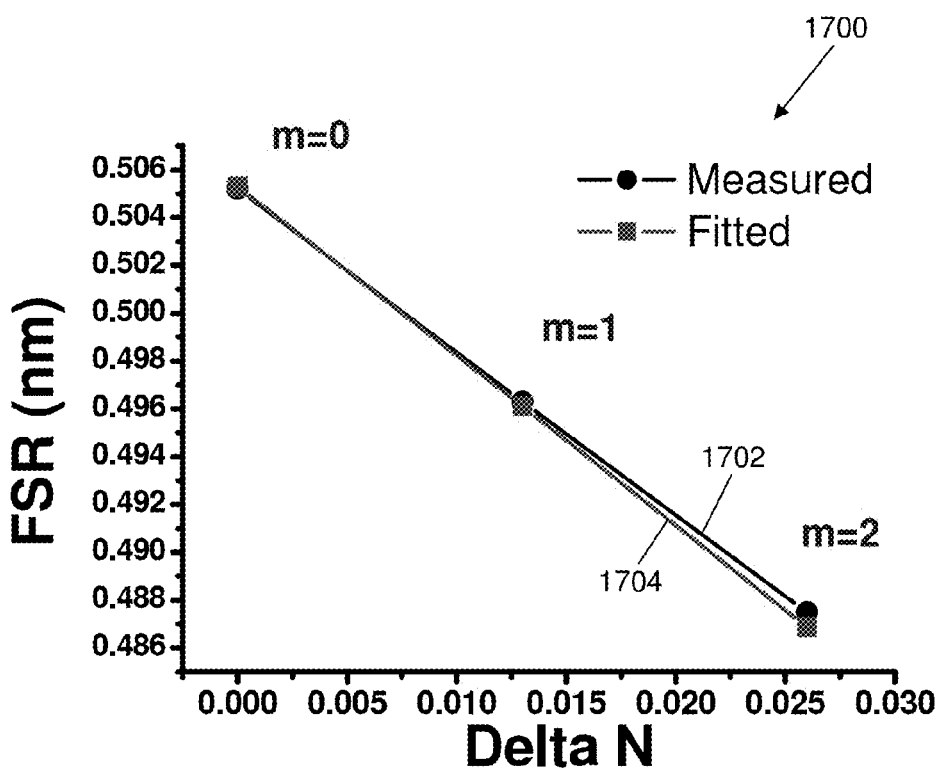
FIG. 17 shows a graph 1700 of a free spectral range (FSR) of an optical circuit plotted against DeltaN according to one embodiment.

FIG. 17 shows a graph 1700 of a free spectral range (FSR) of an optical circuit (e.g. optical circuit 400) plotted against DeltaN. In one embodiment, DeltaN=mΔn, where m=0, 1, 2, . . . , m. Graph 1700 shows a plot 1702 of measured free spectral range of the optical circuit plotted against DeltaN. Graph 1700 shows a plot 1704 of simulated free spectral range of the optical circuit plotted against DeltaN. It can be observed that the measured free spectral ranges and the simulated free spectral ranges at different values of DeltaN have a slight difference.

Figure 18:
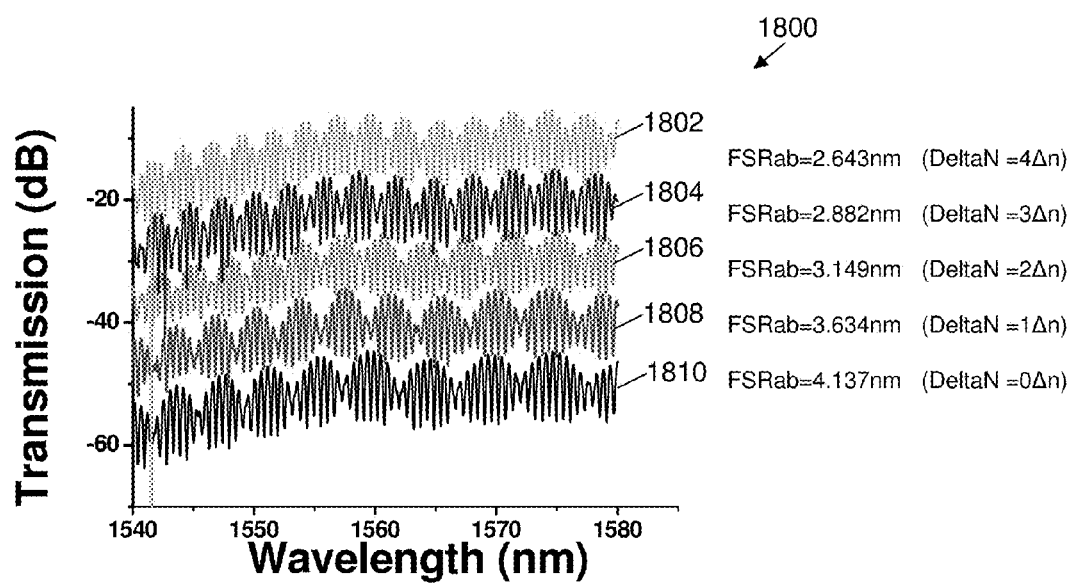
FIG. 18 shows a graph of transmission power of an optical circuit plotted against a wavelength of an optical signal according to one embodiment.

FIG. 18 shows a graph 1800 of transmission power of an optical circuit (e.g. optical circuit 600) plotted against a wavelength of an optical signal. In one embodiment, DeltaN=mΔn, where m=0, 1, 2, . . . , m. FSRab represents a difference between a free spectral range of a sensing arrangement and a free spectral range of a further sensing arrangement.

Graph 1800 shows a plot 1802 for the optical circuit having FSRab=2.643 nm and DeltaN=4Δn. Graph 1800 shows a plot 1804 for the optical circuit having FSRab=2.882 nm and DeltaN=3Δn. Graph 1800 shows a plot 1806 for the optical circuit having FSRab=3.149 nm and DeltaN=2Δn. Graph 1800 shows a plot 1808 for the optical circuit having FSRab=3.634 nm and DeltaN=1Δn. Graph 1800 shows a plot 1810 for the optical circuit having FSRab=4.137 nm and DeltaN=0Δn.

Figure 19:
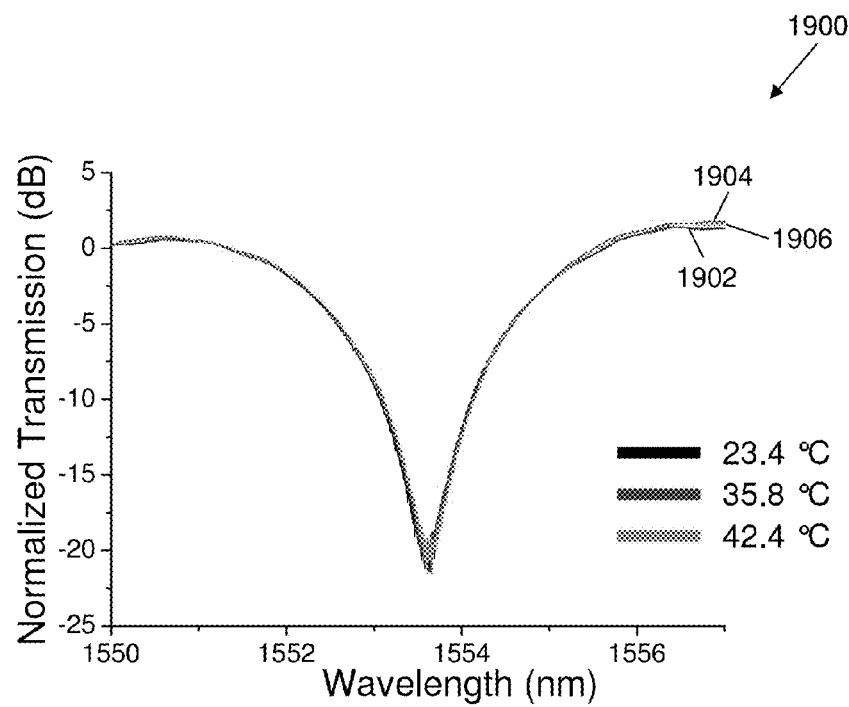
FIG. 19 shows a graph of normalized output of an optical circuit plotted against a wavelength of an optical signal according to one embodiment.

FIG. 19 shows a graph 1900 of normalized output of an optical circuit (e.g. optical circuit 600) plotted against a wavelength of an optical signal. Graph 1900 shows a plot 1902 for the optical circuit when the temperature is about 23.4° C., a plot 1904 for the optical circuit when the temperature is about 35.8° C. and a plot 1906 for optical circuit when temperature is about 42.4° C.

In one embodiment, the optical circuit may be an athermal slot waveguide refractive index biosensor in which no special active component is needed for thermal compensation. Both high sensitivity and temperature/thermal independence can be realized at the same time. The results as described above show that the optical circuits can work with high sensitivity while keep thermal independence. Temperature influence can be reduced in accordance with the refractive indices of the reference waveguide and the waveguide and the lengths of the reference waveguide and the waveguide.

In one embodiment, the optical circuit may be based on cascaded MZI on silicon nitride slot waveguide system which has a smaller thermal optical effect and a lower transmission loss.

In one embodiment, the optical circuit can be applied in applications of silicon waveguide photonics.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

What is claimed is:

1. An optical circuit for sensing a biological entity in a fluid, comprising:
    a sensing arrangement comprising:
    a reference arm having a reference waveguide;
    a sensing arm having a waveguide;
    a sensing window extending across the reference arm and the sensing arm; and
    a further sensing arrangement coupled to the sensing arrangement, the further sensing arrangement comprising:
    a reference arm having a reference waveguide; and
    a sensing arm having a waveguide;
    wherein lengths of the reference waveguide and the waveguide of the sensing arrangement are configured in accordance with a temperature dependency reduction criterion, and
    wherein the further sensing arrangement is covered with a cladding layer.

2. The optical circuit of claim 1, wherein the lengths of the reference waveguide and the waveguide of the sensing arrangement are further configured in accordance with refractive indices of the reference waveguide and the waveguide of the sensing arrangement.

3. The optical circuit of claim 1, wherein the sensing arm of the sensing arrangement further comprises a further waveguide coupled in series with the waveguide of the sensing arrangement.

4. The optical circuit of claim 3, wherein a length of the further waveguide is configured in accordance with the temperature dependency reduction criterion.

5. The optical circuit of claim 4, wherein the length of the further waveguide is further configured in accordance with the refractive index of the reference waveguide, the refractive index of the waveguide and a refractive index of the further waveguide of the sensing arrangement.

6. The optical circuit of claim 1, wherein the reference waveguide of the sensing arrangement comprises a core layer disposed above a first cladding layer and a second cladding layer disposed above the core layer and the first cladding layer.

7. The optical circuit of claim 1,
    wherein the waveguide of the sensing arrangement comprises a core layer disposed above a cladding layer;
    wherein the core layer of the waveguide of the sensing arrangement comprises a first portion and a second portion; and
    wherein the first portion is arranged adjacent to the second portion such that a slot is formed between the first portion and the second portion such that the waveguide of the sensing arrangement constitutes a slot waveguide.

8. The optical circuit of claim 3, wherein the further waveguide comprises a core layer disposed above a first cladding layer and a second cladding layer disposed above the core layer and the first cladding layer.

9. The optical circuit of claim 1, wherein the sensing arrangement further comprises:
    an input port coupled to a first end of the reference arm and a first end of the sensing arm of the sensing arrangement; and
    an output port coupled to a second end of the reference arm and a second end of the sensing arm of the sensing arrangement.

10. The optical circuit of claim 9,
    wherein the input port is configured to direct an optical signal to the first end of the reference arm and the first end of the sensing arm of the sensing arrangement; and wherein the output port is configured to combine an optical signal from the second end of the reference arm and an optical signal from the second arm of the sensing arrangement and to output the combined optical signal.

11. The optical circuit of claim 1, wherein the lengths and cross-sectional areas of the reference arm and the sensing arm of the further sensing arrangement are configured based on the temperature dependency reduction criterion.

12. The optical circuit of claim 11,
wherein the lengths and the cross-sectional areas of the reference arm and the sensing arm of the further sensing arrangement are further configured based on Vernier effect whereby the lengths and the cross-sectional areas of the reference arm and the sensing arm of the further sensing arrangement are further configured based on a free spectral range of the sensing arrangement and a free spectral range of the further sensing arrangement.

13. A method of configuring an optical circuit for sensing a biological entity in a fluid, the optical circuit comprising:
a sensing arrangement comprising a reference arm having a reference waveguide, a sensing arm having a waveguide, and a sensing window extending across the reference arm and the sensing arm, and
a further sensing arrangement coupled to the sensing arrangement, the further sensing arrangement comprising a reference arm having a reference waveguide, and a sensing arm having a waveguide, wherein the further sensing arrangement is covered with a cladding layer
the method comprising:
determining lengths of the reference waveguide and the waveguide of the sensing arrangement based on a temperature dependency reduction criterion.

14. The method of claim 13, wherein the temperature dependency reduction criterion is to minimize the temperature dependency of the optical circuit.

15. The method of claim 14, wherein the temperature dependency of the optical circuit is minimized to zero.

16. The method of claim 13, further comprising determining the lengths of the reference waveguide and the waveguide of the sensing arrangement based on refractive indices of the reference waveguide and the waveguide of the sensing arrangement.

17. The method of claim 13,
wherein the sensing arm of the sensing arrangement of the optical circuit further includes a further waveguide coupled in series with the waveguide of the sensing arrangement; and
wherein the method further comprises determining a length of the further waveguide based on the temperature dependency reduction criterion.

18. The method of claim 17, further comprising determining the length of the further waveguide based on the refractive index of the reference waveguide, the refractive index of the waveguide and a refractive index of the further waveguide.

19. The method of claim 13,
wherein the method further comprises:
determining lengths and cross-sectional areas of the reference arm and the sensing arm of the further sensing arrangement based on the temperature dependency reduction criterion, and
determining the lengths and the cross-sectional areas of the reference arm and the sensing arm of the further sensing arrangement based on Vernier effect.

20. The method of claim 19, wherein determining the lengths and the cross-sectional areas of the reference arm and the sensing arm of the further sensing arrangement based on Vernier effect comprises determining the lengths and the cross-sectional areas of the reference arm and the sensing arm of the further sensing arrangement based on a free spectral range of the sensing arrangement and a free spectral range of the further sensing arrangement.

* * * * *